(12) United States Patent
Lee et al.

(10) Patent No.: US 9,796,827 B2
(45) Date of Patent: Oct. 24, 2017

(54) ESTER PLASTICIZER COMPOSITION

(71) Applicants: Mi Yeon Lee, Daejeon (KR); Sung Shik Eom, Daejeon (KR); Dong Hyun Ko, Daejeon (KR); O Hak Kwon, Daejeon (KR); Da Won Jung, Daejeon (KR); Gyu Il Lee, Daejeon (KR)

(72) Inventors: Mi Yeon Lee, Daejeon (KR); Sung Shik Eom, Daejeon (KR); Dong Hyun Ko, Daejeon (KR); O Hak Kwon, Daejeon (KR); Da Won Jung, Daejeon (KR); Gyu Il Lee, Daejeon (KR)

(73) Assignee: LG Chem, Ltd., Seoul (KR)

(*) Notice: Subject to any disclaimer, the term of this patent is extended or adjusted under 35 U.S.C. 154(b) by 556 days.

(21) Appl. No.: 13/934,883

(22) Filed: Jul. 3, 2013

(65) Prior Publication Data
US 2015/0007750 A1   Jan. 8, 2015

(51) Int. Cl.
*C08K 5/00* (2006.01)
*C08K 5/12* (2006.01)
*C07C 69/82* (2006.01)

(52) U.S. Cl.
CPC ............. *C08K 5/12* (2013.01); *C07C 69/82* (2013.01)

(58) Field of Classification Search
CPC .................................. C08K 5/12; C07C 69/82
USPC ............................................. 106/287.24, 505
See application file for complete search history.

(56) References Cited

U.S. PATENT DOCUMENTS

2008/0058450 A1   3/2008   Stimpson et al.
2010/0305255 A1   12/2010   Grass

FOREIGN PATENT DOCUMENTS

| KR | 100868194 B1 | 11/2008 | |
| KR | WO2008140177 | * 11/2008 | .............. C08L 31/08 |
| KR | 1020080105341 A | 12/2008 | |
| KR | 1020100116176 A | 10/2010 | |
| KR | 10-2013-0035493 | 4/2013 | |

* cited by examiner

*Primary Examiner* — Alexander Polyansky
(74) *Attorney, Agent, or Firm* — Dentons US LLP

(57) ABSTRACT

Disclosed is an ester plasticizer composition, as a plasticizer composition, which comprises a hybrid alkyl-substituted terephthalate compound and a non-hybrid alkyl-substituted terephthalate compound as active ingredients, improves workability due to high absorption speed for the resins and short melting time, and thus may imparts a uniform foaming property upon being applied to wallpaper formulation.

11 Claims, No Drawings

ESTER PLASTICIZER COMPOSITION

BACKGROUND OF THE INVENTION

Field of the Invention

The present invention relates to an ester plasticizer composition. More specifically, the present invention relates to an ester plasticizer composition, as a plasticizer composition, which comprises a hybrid alkyl-substituted terephthalate compound and a non-hybrid alkyl-substituted terephthalate compound as active ingredients, improves workability due to high absorption speed for the resins and short melting time, and thus may imparts a uniform foaming property upon being applied to wallpaper formulation.

Description of the Related Art

In general, a plasticizer forms an ester which reacts an alcohol with a polycarboxylic acid such as phthalic acid and adipic acid.

Examples of commercially important plasticizers include adipates of C8 alcohol, C9 alcohol and C10 alcohols, for example di(2-ethylhexyl)adipate, diisononyl adipate and diisodecyl adipate; and phthalates of C8 alcohol, C9 alcohol and C10 alcohols, for example, di(2-ethylhexyl)phthalate, diisononyl phthalate, and diisodecyl phthalate.

Specifically, the diisononyl phthalate is a plasticizer having a general purpose for polyvinyl chloride (PVC) both through plastisol and dry blending, uses flexible PVC almost all known applications. Typical applications are toys, films, shoes, paints, flooring materials, gloves, wallpaper, artificial leathers, sealants, tarpaulins, car floor coatings, furniture, foam mats, and soundproof panels, all of which are based on plasticity of all PVC. This is also used as a sheath and an insulating material for PVC cables, and to produce other calendered flexible PVC products.

Diisononyl adipate is primarily used in films and is used at a low level in other products such as plastic PVC-based wallpaper, artificial leather, car floor coatings, gloves and sealants. When used in low-temperature product, and/or when using plastisol as an process intermediate, diisononyl adipate is used especially.

Apart from diisononyl adipate, a great deal of research associated with eco-friendly plasticizers continues due to environmental issues of phthalate-based plasticizers.

SUMMARY OF THE INVENTION

Therefore, during continued research associated with eco-friendly plasticizers, the present inventors have found that a plasticizer composition comprising a hybrid alkyl-substituted terephthalate compound and a non-hybrid alkyl-substituted terephthalate compound as active ingredients is to make sure that it is possible to provide an effect that has high absorption speed for the resins and short melting time, improves workability and thus may impart a uniform foaming property upon being applied to wallpaper formulation to the completion of the present invention, based on this discovery.

That is, object of the present invention is to provide an ester plasticizer composition comprising a hybrid alkyl-substituted terephthalate compound and a non-hybrid alkyl-substituted terephthalate compound as active ingredients and as an eco-friendly plasticizer.

In accordance with one aspect of the present invention, is provided an ester plasticizer composition comprising a hybrid alkyl-substituted terephthalate compound and a non-hybrid alkyl-substituted terephthalate compound as active ingredients.

DETAILED DESCRIPTION OF THE INVENTION

Hereinafter, the present invention will be described in detail.

The hybrid alkyl-substituted terephthalate compound constituting the ester plasticizer composition of the present invention include, but are not limited to, generated by the reaction of an alcohol and an acid, the alcohol is a technical feature that it is a mixture of a non-branched primary alcohol having 3 to 4 carbon atoms and a branched primary alcohol having 8 to 10 carbon atoms.

In particular, the hybrid alkyl-substituted terephthalate compound is the most preferred that considering the absorption of the resin and migration lose, it is use a type which is represented by the following Formula 1.

[Formula 1]

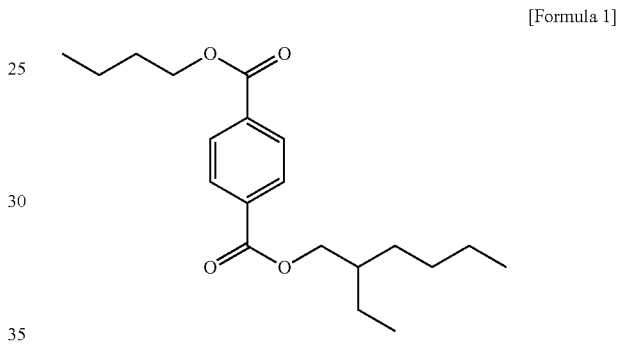

Further, the non-hybrid alkyl-substituted terephthalate compound constituting the ester plasticizer composition of the present invention may be used to blend the non-branched primary alcohol-derived terephthalate compound and the branched primary alcohol-derived terephthalate compound.

The non-hybrid alkyl-substituted terephthalate compounds include, but are not limited to, be prepared by the reaction of an alcohol and an acid, the alcohol is a technical feature that comprises at least one of an non-branched primary alcohol having 3 to 4 carbon atoms and a branched primary alcohol having 8 to 10 carbon atoms. Of these, it is more preferable that the non-branched primary alcohol may be an n-butyl alcohol and the branched primary alcohol may be 2-ethylhexanol.

In particular, it is more preferable that the non-hybrid alkyl-substituted terephthalate compound comprises, as the alcohols, both a compound obtained from an non-branched primary alcohol having 3 to 4 carbon atoms and a compound obtained from a branched primary alcohol having 8 to 10 carbon atoms, in view of ease of processing (plasticizing efficiency) according to high absorption speed of the resin and migration loss.

The acid used in the present invention includes carboxylic acid, polycarboxylic acid or an anhydride thereof, but not limited thereto, is more preferably terephthalic acid.

Furthermore, the acid is preferably in the range of an average particle size of 30 to 100 μm by wet grinding, in view of improving productivity by reducing the response time, wherein the wet grinding, is limited to, be performed preferably using a high-speed rotation wet grinder selected from CAVITRON and TRIGONAL. The rotation may be applied to 3,000 to 50,000 rpm and thus advantageously to reach a quickly desired average particle size distribution.

Meanwhile, a mixing ratio of the non-branched primary alcohol-derived terephthalate compound and the branched primary alcohol-derived terephthalate compound according to the present invention is preferably a weight ratio of 25:75 to 10:90, more preferably 40:60 to 30:70, most preferably about 50:50, in view of absorption speed of the resin.

The non-hybrid alkyl-substituted terephthalate compound obtained by using an non-branched primary alcohol is most preferably used a type which is represented by the following Formula 2.

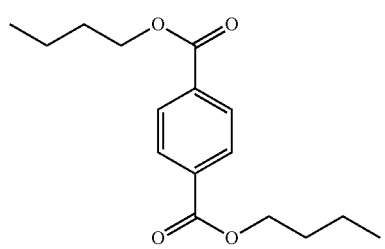

[Formula 2]

Further, the non-hybrid alkyl-substituted terephthalate compound obtained by using the branched primary alcohol is most preferably used a type which is a compound represented by the following Formula 3.

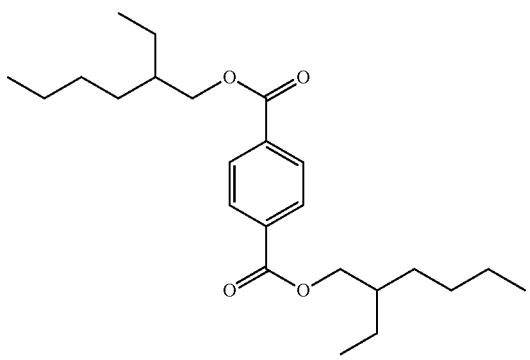

[Formula 3]

The hybrid alkyl-substituted terephthalate compound and the non-hybrid alkyl-substituted terephthalate compound of the present invention may be preferably mixed in a weight ratio of 50:50 to 10:90, in view of improvement in processability and foaming properties.

Further, the hybrid alkyl-substituted terephthalate compound and the non-hybrid alkyl-substituted terephthalate compound of the present invention comprise the compound represented by Formula 1 as the hybrid alkyl-substituted terephthalate compound and compounds of Formulas 2, 3 as the non-hybrid alkyl-substituted terephthalate compound, wherein a mixing ratio of the compound of Formula 1, the compound of Formula 2 and the compound of Formula 3 is preferably a weight ratio of 10 to 50:10 to 50:40 to 80 and is more preferably 30 to 50:10 to 20:40 to 50, in view of processability and foaming properties.

Meanwhile, the ester plasticizer composition of the present invention may be obtained by separately preparing a hybrid alkyl-substituted terephthalate compound and a non-hybrid alkyl-substituted terephthalate compound, followed by mixing, or may be used a mixture itself of a hybrid alkyl-substituted terephthalate compound and a non-hybrid alkyl-substituted terephthalate compound obtained through esterification reaction between terephthalic acid and a mixture of suitable alcohols.

These ester plasticizer compositions include, but are not limited to, be applied preferably as a plasticizer for vinyl chloride resins. The ester plasticizer composition may be used in the range of 5 to 100 parts by weight, per 100 parts by weight of a vinyl chloride resin. In this case, the ester plasticizer composition may comprise additional plasticizer selected from dioctyl phthalate (DOP), dibutyl phthalate (DBP), dioctyl terephthalate (DOTP), diisononyl phthalate (DINP), and diisodecyl phthalate (DIDP), in the range of 5 to 100 parts by weight per 100 parts by weight of the resin.

In addition, but not limited to, the composition of the present invention may further comprise 0.5 to 7 parts by weight of a stabilizer, and 0.5 to 3 parts by weight of a lubricant.

In particular, as can has been elucidated in the following Examples, the ester plasticizer composition provides uniform foaming properties when applied to wallpaper formulation.

EXAMPLE

Now, the present invention will be described in more detail with reference to the following examples. These examples are only provided to illustrate the present invention and should not be construed as limiting the scope and spirit of the present invention.

Example 1

First, a terephthalic acid was prepared as a pulverized product having the average particle size in the range of 30 to 100 μm. 440 g of prepared pulverized sterephthalic acid, 297 g of n-butanol and 530 g of 2-ethylhexanol were reacted at 200° C. for 3 hours, the reaction mixture was neutralized with Na2CO3, washed once with water, and was removed alcohol by heating under reduced pressure to obtain a plasticizer composition.

The obtained plasticizer was analyzed by a GC-mass analyzer. As a result, it was confirmed to be composed of chemicals represented by the following Formulas 1, 2 and 3.

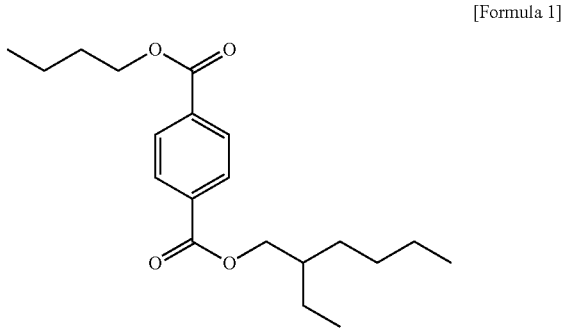 [SMILES: CCCCOC(=O)c1ccc(C(=O)OCC(CC)CCCC)cc1]

[Formula 1]

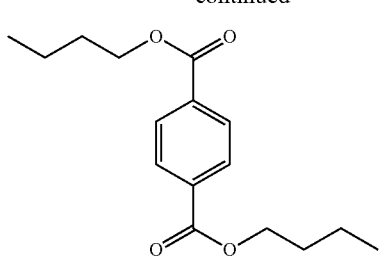

[Formula 2]

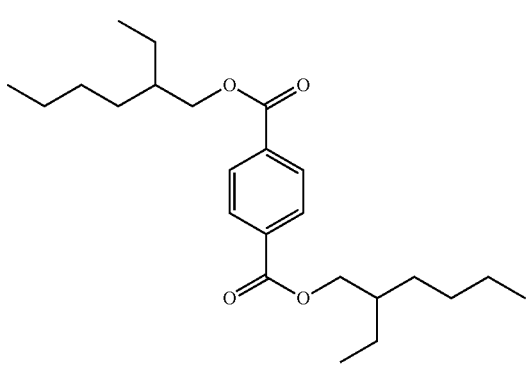

[Formula 3]

In addition, it was confirmed that a weight ratio of the compound of Formula 1, the compound of Formula 2 and the compound of Formula 3 was 50:10:40.

The reaction product was used in the range of 5 to 100 parts by weight, per 100 parts by weight of the vinyl chloride resin. A stabilizer, a lubricant and a foaming agent were further added to the product, followed by extrusion molding to produce wallpaper.

The wallpaper exhibited a 10% decrease in absorption speed [mixing time measured under conditions (77° C., 60 rpm/PVC (LS 100) 400 Plasticizer 200 g)] during production, as compared to a case of using DOP alone, and a similar melting rate (when measured at 110° C./55 g/60 rpm), as compared to a case of using DOP alone and a 50% decrease in melting rate, as compared to a case of using DOTP alone.

Regarding foaming properties of produced wallpaper, cells after foaming were observed with an optical microscope. As a result, it was seen that the size, shape and array of the cells were uniform, as compared to cases of using DOP, DINP or DOTP, respectively.

Example 2

Except that it was used by mixing a compound represented by the Formula 1 of 30 parts by weight, a compound represented by the Formula 2 of 10 parts by weight and a compound represented by the Formula 3 of 60 parts by weight in Example 1, wallpaper was produced in the same manner as in Example 1.

The wallpaper exhibited a similar absorption speed [mixing time measured under conditions (77° C., 60 rpm/PVC (LS 100) 400 Plasticizer 200 g)] during production, as compared to a case of using DOP alone, and a 25% decrease in absorption speed, as compared to a case of using DOTP alone and a 37% decrease in melting rate (when measured under conditions of 110° C./55 g/60 rpm), as compared to a case of using DOTP alone.

Regarding foaming properties of the produced wallpaper, cells after foaming were observed with an optical microscope. As a result, it was seen that the size, shape and array of the cells were uniform, as compared to cases of using DOP, DINP or DOTP, respectively.

Comparative Example 1

Except that 440 g of terephthalic acid and 890 g of n-butanol were reacted for 13 hours under 130° C. to in Example 1, a plasticizer was prepared in the same manner as Example 1.

The obtained plasticizer was analyzed with a GC mass analyzer. As a result, it was identified that the plasticizer comprised the compound of the following Formula 2.

[Formula 2]

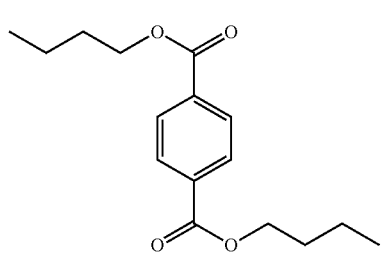

The compound was used in the range of 5 to 100 parts by weight, per 100 parts by weight of the vinyl chloride resin. A stabilizer, a lubricant and a foaming agent were further added to the product, followed by extrusion molding to produce wallpaper.

The wallpaper exhibited a 67% decrease in absorption speed [mixing time measured under conditions (77° C., 60 rpm/PVC (LS 100) 400 Plasticizer 200 g)] during production, as compared to a case of using DOP alone, and a 31% decrease in melting rate (when measured under conditions of 110° C./55 g/60 rpm), as compared to a case of using DOP alone.

Further, as compared to the case of using DOP alone, the wallpaper exhibited a 7% increase in migration loss (migration loss of plasticizer measured after heating at 80° C. for 72 hours).

Regarding foaming properties of the produced wallpaper, cells after foaming were observed with an optical microscope. As a result, it was seen that the size, shape and array of the cells were uniform, as compared to cases of using DOP, DINP or DOTP, respectively.

Comparative Example 2

Except that 440 g of terephthalic acid and 1,060 g of 2-ethylhexanol were reacted under 220° C. for 5 hours in Example 1, a plasticizer was prepared in the same manner as in Example 1.

The obtained plasticizer was analyzed with a GC-mass analyzer. As a result, it was identified that the plasticizer comprised a compound of the following Formula 3.

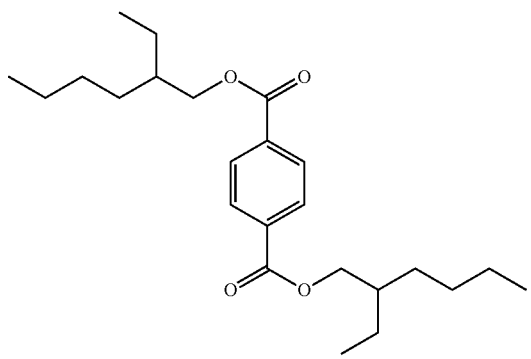

[Formula 3]

The compound was used in the range of 5 to 100 parts by weight, per 100 parts by weight of the vinyl chloride resin. A stabilizer, a lubricant and a foaming agent were further added to the product, followed by extrusion molding to produce wallpaper.

The wallpaper exhibited a 28% increase in absorption speed [mixing time measured under conditions (77° C., 60 rpm/PVC (LS 100) 400 Plasticizer 200 g)] during production, as compared to a case of using DOP alone, and a 76% increase in melting rate (when measured under conditions of 110° C./55 g/60 rpm), as compared to a case of using DOP alone.

As compared to the case of using DOP alone, the wallpaper exhibited a 1% decrease in migration loss.

Further, regarding foaming properties of the produced wallpaper, cells after foaming were observed with an optical microscope. As a result, it was seen that the size, shape and array of the cells were inferior, as compared to cases of using DOP, DINP, DBTP or BPTP, respectively.

As can be confirmed from the measurement results described above, Comparative Example 1 in which the compound of Formula 2 was used alone exhibited significant reduction in absorbed and molten surface, but was disadvantageously exhibited serious migration.

Further, Comparative Example 2 in which the compound of Formula 3 was used alone do not occur almost migrated, but disadvantageously takes a lot time when absorbed and melted as the higher molecular weight.

Meanwhile, as in Examples 1 and 2, when comprised all compounds even with proper mixing ratio, it was confirmed the preferred results in the physical properties of all surfaces.

As apparent from the above description, the present invention provides an ester plasticizer composition, which comprises a hybrid alkyl-substituted terephthalate compound and a non-hybrid alkyl-substituted terephthalate compound as active ingredients, advantageously improves workability due to high absorption speed for the resins and short melting time, and thus may impart a uniform foaming property upon being applied to wallpaper formulation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An ester plasticizer composition comprising a hybrid alkyl-substituted terephthalate compound and a non-hybrid alkyl-substituted terephthalate compound as active ingredients,
wherein the non-hybrid alkyl-substituted terephthalate compound comprises at least one of a non-branched primary alcohol-derived terephthalate compound and a branched primary alcohol-derived terephthalate compound,
wherein the hybrid alkyl-substituted terephthalate compound is represented by following Formula 1,
wherein the non-branched primary alcohol-derived terephthalate compound is represented by following Formula 2, and
wherein the branched primary alcohol-derived terephthalate compound is represented by following Formula 3:

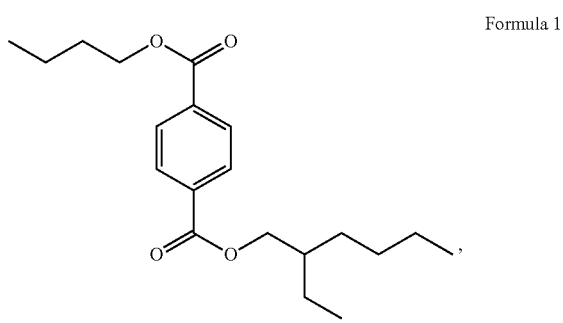

Formula 1

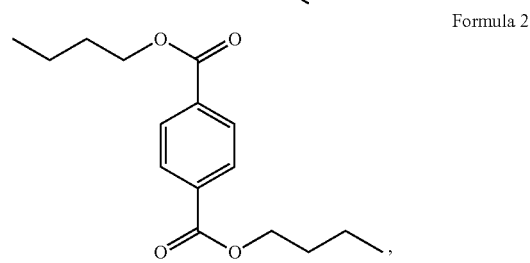

Formula 2

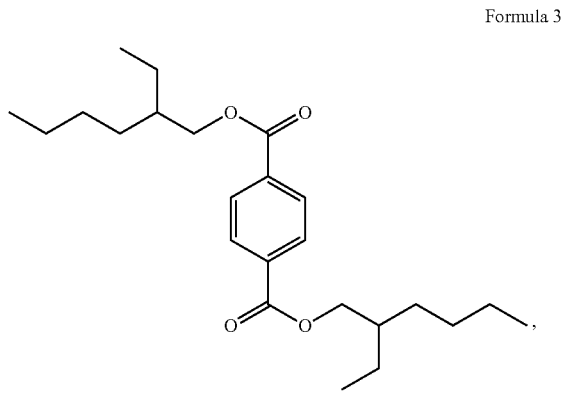 [SMILES: CCCCC(CC)COC(=O)c1ccc(C(=O)OCC(CC)CCCC)cc1]

Formula 3 and
wherein the non-hybrid alkyl-substituted terephthalate compound and the hybrid alkyl-substituted terephthalate compound are generated by the reaction of an acid with a mixture of n-butanol and 2-ethylhexanol.

2. The ester plasticizer composition according to claim 1, wherein the acid is terephthalic acid.

3. The ester plasticizer composition according to claim 1, wherein the acid has an average particle size of 30 to 100 μm.

4. The ester plasticizer composition according to claim 1, wherein a mixing ratio of the non-branched primary alcohol-derived terephthalate compound and the branched primary alcohol-derived terephthalate compound is a weight ratio of 25:75 to 10:90.

5. The ester plasticizer composition according to claim 1, wherein a mixing ratio of the hybrid alkyl-substituted terephthalate compound and the non-hybrid alkyl-substituted terephthalate compound is a weight ratio of 50:50 to 10:90.

6. The ester plasticizer composition according to claim 1, wherein a mixing ratio of the compound represented by Formula 1, the compound represented by Formula 2 and the compound represented by Formula 3 is a weight ratio of 10 to 50:10 to 50:40 to 80.

7. The ester plasticizer composition according to claim 1, wherein the ester plasticizer composition is used as a plasticizer for vinyl chloride resins.

8. The ester plasticizer composition according to claim 7, wherein the ester plasticizer composition is used in the range of 5 to 100 parts by weight, per 100 parts by weight of the vinyl chloride resin.

9. The ester plasticizer composition according to claim 7, wherein the ester plasticizer composition is used as a plasticizer for wallpaper application.

10. The ester plasticizer composition according to claim 5, wherein the acid is terephthalic acid.

11. The ester plasticizer composition according to claim 5, wherein the acid has an average particle size of 30 to 100 μm.

* * * * *